United States Patent [19]

Gers-Barlag et al.

[11] Patent Number: 5,788,952

[45] Date of Patent: Aug. 4, 1998

[54] COSMETIC AND DERMATOLOGICAL PHOTOPROTECTIVE FORMULATIONS CONTAINING INORGANIC MICROPIGMENTS

[75] Inventors: Heinrich Gers-Barlag, Kummerfeld; Sabine Schulz, Hamburg, both of Germany

[73] Assignee: Beiersdorf AG, Hamburg, Germany

[21] Appl. No.: 495,641

[22] PCT Filed: Jan. 20, 1994

[86] PCT No.: PCT/DE94/00041

§ 371 Date: Aug. 4, 1995

§ 102(e) Date: Aug. 4, 1995

[87] PCT Pub. No.: WO94/17779

PCT Pub. Date: Aug. 18, 1994

[30] Foreign Application Priority Data

Feb. 11, 1993 [DE] Germany .................. 43 03 983.9

[51] Int. Cl.$^6$ .................. A61K 7/42; A61K 7/00
[52] U.S. Cl. .................. 424/59; 424/60; 424/400; 424/401
[58] Field of Search .................. 424/59, 60, 400, 424/401

[56] References Cited

U.S. PATENT DOCUMENTS 5,538,716   7/1996   Forestier et al. .................. 424/59

*Primary Examiner*—Shelly A. Dodson
*Attorney, Agent, or Firm*—Sprung Kramer Schaefer & Briscoe

[57] ABSTRACT

Cosmetic and dermatological sunscreen formulations containing (a) inorganic micropigments as UV filter substances and (b) optionally additional organic UV filter substances characterized in that (c) the formulations are hydrodispersions (d) which consist of an inner lipid and an outer aqueous phase, and (e) which are essentially free of emulsifiers, and in that (f) the inorganic micropigments are incorporated in the lipid phase of the hydrodispersions.

8 Claims, No Drawings

COSMETIC AND DERMATOLOGICAL PHOTOPROTECTIVE FORMULATIONS CONTAINING INORGANIC MICROPIGMENTS

DESCRIPTION

The present invention relates to cosmetic and dermatological sunscreen preparations, in particular skin-caring cosmetic and dermatological sunscreen preparations.

The damaging effect of the ultraviolet part of solar radiation on the skin is generally known. While rays having a wavelength which is smaller than 290 nm (the so-called UVC range) are absorbed by the ozone layer in the earth's atmosphere, rays in the range between 290 nm and 320 nm, the so-called UVB range, cause erythema, simple sunburn or even more or less severe burns.

The relatively narrow range around 308 nm is indicated as a maximum of the erythema activity of sunlight.

For protection against UVB radiation, numerous compounds are known which are mostly derivatives of 3-benzylidenecamphor, of 4-aminobenzoic acid, of cinnamic acid, of salicylic acid, of benzophenone and also of 2-phenylbenzimidazole.

Even for the range between approximately 320 nm and approximately 400 nm, the so-called UVA range, it is important to have available filter substances, as even its rays can produce damage. It has thus been shown that UVA radiation leads to damage to the elastic and collagenic fibres of the connective tissue, which can prematurely age the skin, and that it is to be regarded as the cause of numerous phototoxic and photoallergic reactions. The damaging effect of the UVB radiation can be increased by UVA radiation.

For protection against the rays of the UVA range, certain derivatives of dibenzoylmethane are therefore used whose photostability (Int. J. Cosm. Science 10, 53 (1988)) is not specified to an adequate extent.

The UV radiation, however, can also lead to photochemical reactions, the photochemical reaction products then intervening in the skin's metabolism.

Mainly, such photochemical reaction products are free-radical compounds, e.g. hydroxyl radicals. Even undefined free-radical photoproducts, which are formed in the skin itself, can have uncontrolled secondary reactions on account of their high reactivity. However, even singlet oxygen, a non-free-radical excited state of the oxygen molecule, can occur on UV irradiation, just like short-lived epoxides and many others. Singlet oxygen, for example, is distinguished compared with the normally present triplet oxygen (free-radical ground state) by increased reactivity. Of course, excited, reactive (free-radical) triplet states of the oxygen molecule also exist.

UV radiation is further counted as ionizing radiation. There is thus the risk that ionic species are also formed on UV exposure, which then for their part are able to intervene oxidatively in the biochemical processes.

In order to prevent these reactions, antioxidants and/or free-radical scavengers can additionally be incorporated into the cosmetic or dermatological formulations.

Most inorganic pigments are UV absorbers or UV reflectors, which, as is known, are used in cosmetics for the protection of the skin from UV rays. These are oxides of titanium, zinc, iron, zirconium, silicon, manganese, aluminium, cerium and mixtures thereof, and also derivatives.

The inorganic pigments are distinguished by good sunscreen action. However, they have the disadvantage that it is difficult to incorporate them into such formulations in a satisfactory manner.

A further disadvantage of the use of inorganic pigments in cosmetic formulations is that such pigments lead in by far the most cases to severe dryness of the skin.

As the pigment particles have to be efficiently prevented from accumulating to give agglomerates, a certain proportion of emulsifiers or comparable surface-active or interface-active substances always had to be added to the formulations.

Per se, the use of the customary cosmetic emulsifiers is harmless. Nevertheless, emulsifiers, in the end like any chemical substance, can produce allergic reactions or reactions based on hypersensitivity of the user in the isolated case.

Thus, it is known that specific photodermatoses are induced by certain emulsifiers, but also by various fats, and simultaneous exposure to sunlight. Such light dermatoses are also termed "Majorca acne". It was therefore an object of the present invention to develop emulsifier-free sunscreen products.

Emulsifier-free sunscreen preparations based on so-called hydrodispersions have been available to the user for some time.

Hydrodispersions are dispersions of a liquid, semi-solid or solid inner (discontinuous) lipid phase in an outer aqueous (continuous) phase.

In contrast to O/W emulsions, which are distinguished by a similar phase arrangement, hydrodispersions, however, are essentially free of emulsifiers. Hydrodispersions are, otherwise also like emulsions, metastable systems and are inclined to change into a state of two mutually coherent discrete phases. In emulsions, the choice of a suitable emulsifier prevents phase separation.

In the case of hydrodispersions of a liquid lipid phase in an outer aqueous phase, the stability of such a system can be guaranteed, for example, in that in the aqueous phase a gel structure is built up in which the lipid droplets are stably suspended.

Although this type of formulation offers the advantage of freedom from emulsifier compared with the conventional sunscreen formulations, on the other hand there are also some points which need improvement. Thus, for a good sunscreen action of such preparations a comparatively high concentration of UV filters is necessary. Moreover, such preparations feel sticky in comparison with emulsions and sunscreen oils.

It was therefore a further object to make available sunscreen preparations which are distinguished by a relatively low concentration of UV filters and moreover impart a pleasant skin sensation. Another object of the present invention was to make available non-sticky sunscreen preparations.

It was surprising and unforeseeable for the person skilled in the art that these objects are achieved by cosmetic and dermatological sunscreen formulations containing (a) inorganic micropigments as UV filter substances and
(b) optionally additional organic UV filter substances characterized in that (c) the formulations are hydrodispersions
(d) which consist of an inner lipid and an outer aqueous phase, and
(e) which are essentially free of emulsifiers, and in that
(f) the inorganic micropigments are incorporated in the lipid phase of the hydrodispersions Sunscreen formulations based on $TiO_2$ pigments are in fact described in the specifications EP-OS 456 458, EP-OS 456 459 and EP-OS 456 460. Emulsifier-free systems, however, cannot be realized in such a manner. Pigment-containing hydrodispersions of the type according to the invention have also not been disclosed hitherto.

It was surprising and unforeseeable that on following the technical teaching hereby disclosed in every respect extremely satisfactory preparations are obtainable. It was rather to have been expected that the micropigment particles, for lack of an emulsifier, would accumulate to give agglomerates.

It was furthermore surprising that the stickiness of the hydrodispersions can be drastically decreased on following the technical teaching hereby disclosed.

Finally, it was surprising that the use of inorganic pigments in the formulations according to the invention does not lead to severe dryness of the skin, but in contrast causes a lasting, extremely pleasant skin sensation.

Cosmetic and dermatological preparations according to the invention preferably contain inorganic pigments based on metal oxides and/or other poorly water-soluble or -insoluble metal compounds, in particular of the oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and mixtures of such oxides. They are particularly preferably pigments based on $TiO_2$.

A prerequisite for the utilizability of inorganic pigments for the purposes according to the invention is of course the cosmetic or dermatological acceptability of the underlying substances.

For the present invention it is essentially insignificant in which modifications such metal oxides are present. $TiO_2$, for example, occurs in nature in three main modifications (rutile, anatase and brookite), which are basically all equally suitable. The same applies to the modifications of the iron oxides etc.

It is advantageous to select particle diameters of the pigments used of less than 100 nm.

It is particularly advantageous within the meaning of the present invention if the inorganic pigments are present in hydrophobic form, i.e. that they have a surface water-repellent treatment. This surface treatment can consist in providing the pigments with a thin hydrophobic layer according to processes known per se.

Such a process consists, for example, in generating the hydrophobic surface layer according to a reaction

n and m here are stoichiometric parameters to be employed as desired, and R and R' are the desired organic radicals. For example, hydrophobized pigments prepared in analogy to DE-OS 33 14 742 are advantageous.

Advantageous $TiO_2$ pigments are obtainable, for example, under the trade names MT 100 T from the company TAYCA.

The cosmetic and/or dermatological sunscreen formulations according to the invention can be made up in the customary manner and can be used for cosmetic and/or dermatological protection from the sun and furthermore for the treatment, the care and the cleansing of the skin and/or the hair and as a make-up product in decorative cosmetics.

For use, the cosmetic and dermatological preparations according to the invention are applied to the skin and/or the hair in adequate amounts in the manner customary for cosmetics.

Particularly preferred cosmetic and dermatological preparations are those which are present in the form of a sunscreen composition. These preferably additionally contain at least one UVA filter and/or at least one further UVB filter and/or at least one inorganic pigment.

The cosmetic and dermatological preparations according to the invention can contain cosmetic auxiliaries, such as are customarily used in such preparations, e.g. preservatives, bactericides, perfumes, substances for preventing foaming, colorants, pigments which have a colouring effect,, thickeners, moisturizing and/or moisture-retaining substances, fats, oils, waxes or other customary constituents of a cosmetic or dermatological formulation such as alcohols, polyols, polymers, foam stabilizers, electrolytes, organic solvents or silicone derivatives.

The lipid phase can advantageously be selected from the following substance group:

oils, such as triglycerides of capric or of caprylic acid, but preferably castor oil;

fats, waxes and other natural and synthetic fatty substances, preferably esters of fatty acids with alcohols of low C number, e.g. with isopropanol, propylene glycol or glycerol, or esters of fatty alcohols with alkanoic acids of low C number or with fatty acids;

silicone oils such as dimethylpolysiloxanes, diethylpolysiloxanes, diphenylpolysiloxanes and mixtures thereof.

It is particularly preferred to select the components of the lipid phase from the silicone oils group.

The aqueous phase of the preparations according to the invention optionally advantageously contains alcohols, diols or polyols of low C number, and also their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, e.g. ethanol, isopropanol, 1,2-propanediol, glycerol and, in particular, one or more thickeners which can be advantageously selected from the group consisting of silica, aluminium silicates, polysaccharides or their derivatives, e.g. hyaluronic acid, xanthan gum, hydroxypropyl-methylcellulose, particularly advantageously from the polyacrylates group, preferably a polyacrylate from the so-called Carbopols group, for example Carbopols of the types 980, 981, 1382, 2984, 5984, in each case individually or in combination.

The cosmetic or dermatological sunscreen preparations contain inorganic pigments e.g. in amounts from 0.1% by weight to 30% by weight, preferably in amounts from 0.5% by weight to 10% by weight, but in particular 1% by weight to 6% by weight, based on the total weight of the preparations.

Apart from the inorganic pigments, it is advantageous according to the invention to employ oil-soluble UVA filters and/or UVB filters in the lipid phase and/or water-soluble UVA filters and/or UVB filters in the aqueous phase.

The sunscreen formulations according to the invention can advantageously contain substances which absorb UV radiation in the UVB range, the total amount of the filter substances being e.g. 0.1% by weight to 30% by weight, preferably 0.5 to 10% by weight, in particular 1 to 6% by weight, based on the total weight of the preparations, in order to make available cosmetic preparations which protect the skin from the entire range of ultraviolet radiation. They can also be used as sunscreen agents.

The UVB filters can be oil-soluble or water-soluble. Advantageous oil-soluble UVB filter substances are e.g.:

3-benzylidenecamphor derivatives, preferably 3-(4-methylbenzylidene) camphor, 3-benzylidenecamphor;

4-aminobenzoic acid derivatives, preferably 2-ethylhexyl 4-dimethylaminobenzoate, amyl 4-dimethylaminobenzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzylidenemalonic acid, preferably di(2-ethylhexyl) 4-methoxybenzylidenemalonate;

2,4,6-trianilino-(p-carbo-2'-ethyl-1'-hexyloxy)-1,3,5-triazine.

Advantageous water-soluble UVB filter substances are e.g.:

salts of 2-phenylbenzimidazole-5-sulphonic acid such as its sodium, potassium or its triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as e.g. 4-(2-oxo-3-bornylidenemethyl) benzenesulphonic acid, 2-methyl-5-(2-oxo-3-bornylidenemethyl)sulphonic acid and its salts.

The list of the UVB filters mentioned, which can be used in combination with the inorganic pigments according to the invention, should obviously be non-limiting.

It can also be advantageous to combine the inorganic pigments according to the invention with UVA filters which to date are customarily contained in cosmetic preparations. These substances are preferably derivatives of dibenzoylmethane, in particular 1-(4'-tert-butylphenyl)-3-(4'-methoxyphenyl)propane-1, 3-dione and 1-phenyl-3-(4'-isopropylphenyl)propane-1,3-dione. These combinations or preparations which contain these combinations are also a subject of the invention. The amounts used for the UVB combination can be employed.

It is furthermore advantageous to combine the inorganic pigments according to the invention with UVA and UVB filters.

The invention also relates to a process for the preparation of the cosmetic and/or dermatological sunscreen preparations according to the invention, which is characterized in that, in a manner known per se, the inorganic pigment is suspended in the preferably liquid lipid phase, in which a thickener has optionally been incorporated, with even stirring and optionally with warming and, if desired, is homogenized, and afterwards the suspension is mixed with the aqueous phase, in which a thickener has optionally been incorporated, and which preferably has approximately the same temperature as the suspension, if desired homogenized and allowed to cool to room temperature. After cooling to room temperature, homogenization can again be carried out, in particular if volatile constituents are additionally to be incorporated.

The present invention also comprises a process for the protection of the skin and the hair from UV radiation, which is characterized in that a cosmetic and/or dermatological sunscreen formulation which contains an effective concentration of inorganic micropigments as UV filter substances and optionally additional organic UV filter substances, the formulations being hydrodispersions which consist of an inner lipid phase and an outer aqueous phase and which are essentially free of emulsifiers, and the inorganic micropigments are incorporated into the lipid phase of the hydrodispersions and applied in an adequate amount to the skin or hair, and the use of these formulations, in particular for these purposes.

The present invention also comprises a process for the protection of colorless or coloured cosmetic or dermatological preparations against UV rays, and also these preparations, characterized in that the preparations contain an effective concentration of inorganic micropigments as UV filter substances and optionally additional organic UV filter substances, the preparations being hydrodispersions which consist of an inner lipid phase and an outer aqueous phase and which are essentially free of emulsifiers, and the inorganic micropigments being incorporated in the lipid phase of the hydrodispersions.

The following examples are intended to illustrate the present invention without restricting it. All quantitative data, proportions and percentages are, if not stated otherwise, based on the weight and the total amount or on the total weight of the preparations.

Example 1

| Sun gel, sun protection factor 12 | % by weight |
|---|---|
| Phenyltrimethicon | 4.50 |
| Carbomer 981 | 1.50 |
| Octyl methoxycinnamate | 7.50 |
| Parsol ® 1789 | 3.00 |
| TiO$_2$, particle size <100 nm | 4.50 |
| Ethanol | 9.00 |
| Glycerol | 4.50 |
| Hydroxypropylmethylcellulose | 0.30 |
| EDTA solution (14% strength) | 0.75 |
| Trisaminopromethamine | 2.01 |
| Perfume, preservatives, colorants | q.s. |
| Water, demineralized | to 100.00 |

Example 2

| Sun gel, sun protection factor 12 | % by weight |
|---|---|
| Octyldodecanol | 4.50 |
| Carbomer 981 | 1.50 |
| Octyl methoxycinnamate | 7.50 |
| Parsol ® 1789 | 3.00 |
| TiO$_2$, particle size <100 nm | 4.50 |
| Ethanol | 9.00 |
| Butylene glycol | 4.50 |
| Hydroxypropylmethylcellulose | 0.30 |
| EDTA solution (14% strength) | 0.75 |
| Trisaminopromethamine | 2.01 |
| Perfume, preservative, colorants | q.s. |
| Water, demineralized | to 100.00 |

Example 3

| Sun gel, sun protection factor 12 | % by weight |
|---|---|
| Castor oil | 4.50 |
| Carbomer 981 | 1.50 |
| Octylmethoxycinnamate | 7.50 |
| Parsol ® 1789 | 3.00 |

-continued

| Sun gel, sun protection factor 12 | % by weight |
|---|---|
| TiO$_2$, particle size <100 nm | 4.50 |
| Ethanol | 9.00 |
| Butylene glycol | 4.50 |
| Hydroxypropylmethylcellulose | 0.30 |
| EDTA solution (14% strength) | 0.75 |
| Trisaminopromethamine | 2.01 |
| Perfume, preservative, colorants | q.s. |
| Water, demineralized | to 100.00 |

We claim:

1. A cosmetic and dermatological sunscreen formulation comprising
   (a) inorganic micropigments, which are hydrophobized on the surface, as UV filter substances and
   (b) optionally additional organic UV filter substances
   wherein
   (c) the formulation is a hydrodispersion
   (d) which consist of an inner lipid and an outer aqueous phase, and
   (e) which are essentially free of emulsifiers, and in that
   (f) the organic micropigments are incorporated in the lipid phase of the hydrodispersion.

2. The formulation according to claim 1, wherein the inorganic micropigments are based on metal oxides and/or another poorly water-soluble or water-insoluble metal compound.

3. The formulation according to claim 2, wherein the inorganic micropigments contains oxides or mixed oxides of metals selected from the group consisting of titanium, zinc, iron, zirconium, silicone, manganese, aluminum, or cerium.

4. The sunscreen formulation according to claim 1, wherein that the aqueous phase of the hydrodispersion contains a thickener.

5. The formulation according to claim 1, wherein the amount of inorganic pigments based upon the total weight of the formulation is 0.01 % by weight to 30% by weight.

6. The formulation according to claim 1, wherein the amount of inorganic pigment based upon the total weight of the formulation is 0.1% by weight to 6% by weight.

7. In a method for protecting the skin from the harmful action of ultraviolet light, the improvement which comprises placing a formulation according to claim 1 on the skin.

8. The formulation according to claim 1, wherein the inorganic micropigment is based upon SiO$_2$.

* * * * *